United States Patent [19]
Saito et al.

[11] Patent Number: 5,583,903
[45] Date of Patent: Dec. 10, 1996

[54] COMPUTED TOMOGRAPHY APPARATUS

[75] Inventors: Yasuo Saito; Kazuyuki Ihira; Hiroaki Miyazaki, all of Tochigi-ken, Japan

[73] Assignee: Kabushiki Kaisha Toshiba, Kawasaki, Japan

[21] Appl. No.: 566,158

[22] Filed: Dec. 1, 1995

[30]     Foreign Application Priority Data

Dec. 6, 1994  [JP]  Japan .................................... 6-302405

[51] Int. Cl.⁶ ............................ A61B 6/03; G01N 23/083
[52] U.S. Cl. ........................................ 378/19; 364/413.15
[58] Field of Search ......................... 378/19; 364/413.15, 364/413.16

[56]              References Cited

U.S. PATENT DOCUMENTS

| | | | |
|---|---|---|---|
| 4,075,484 | 2/1978 | Meyer-Ebrecht et al. | 378/9 |
| 4,995,107 | 2/1991 | Klingenbeck | 378/7 |
| 5,253,170 | 10/1993 | Kanamori et al. | 364/413.16 |
| 5,430,785 | 7/1995 | Pfoh et al. | 378/19 |

*Primary Examiner*—David P. Porta
*Assistant Examiner*—David Vernon Bruce
*Attorney, Agent, or Firm*—Oblon, Spivak, McClelland, Maier & Neustadt, P.C.

[57]              ABSTRACT

In a computed tomography apparatus which irradiates an X-ray ray fan beam to a slice of a subject body from various directions around the slice, detects the image data of the X-ray ray that has passed the subject body to obtain projection data, and performs reconstruction computation on the projection data to acquire the tomographic image of the slice of the subject body, a main detector which has a plurality of rows of detection elements are aligned in association with a plurality of slices of the subject body and detects projection data of a plurality of slices at a time, a profile detector which has the same number of rows of detection elements as the main detector and measures a profile in the slice direction of the amount of X-ray ray incident to the main detector, and a data processing device for compensating the projection data output from the main detector in accordance with the output of the profile detector.

14 Claims, 5 Drawing Sheets

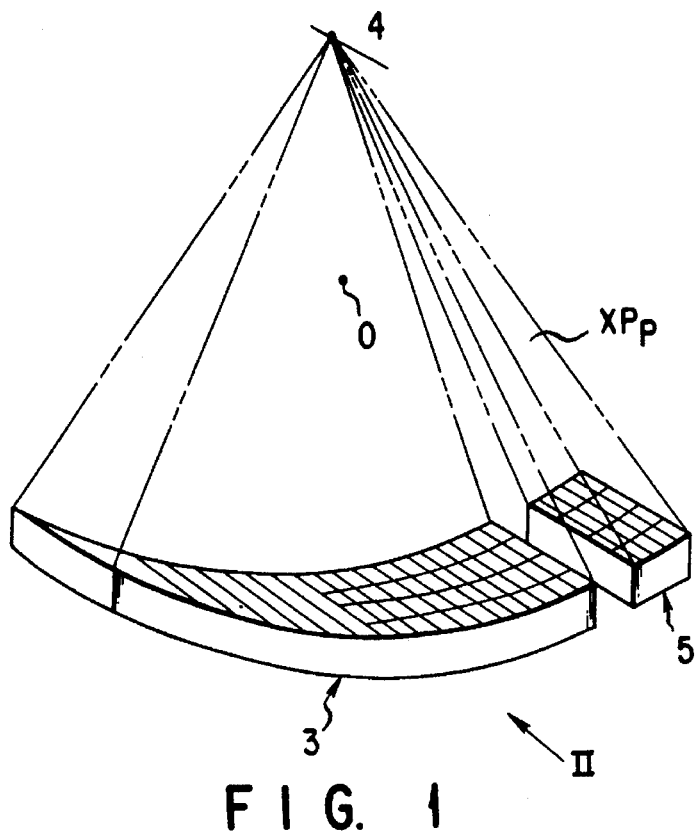
F I G. 1
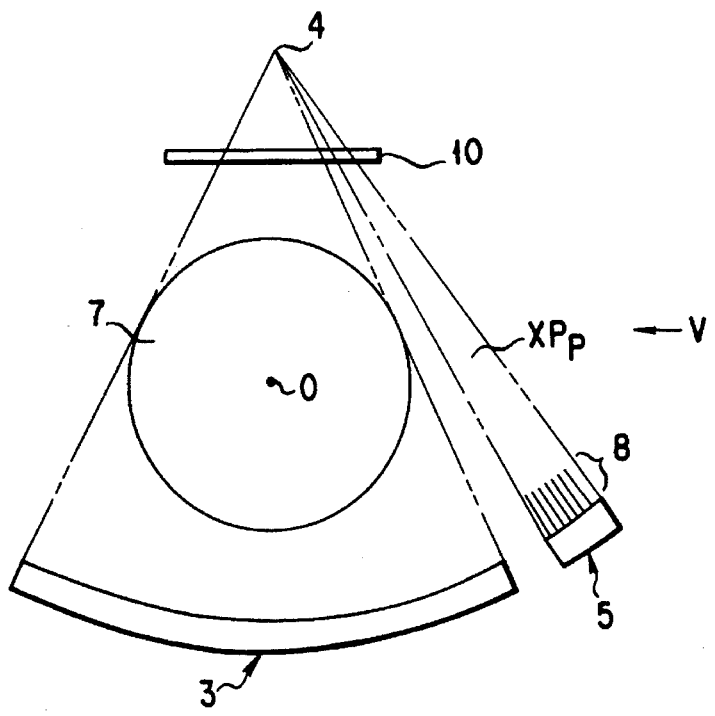
F I G. 2

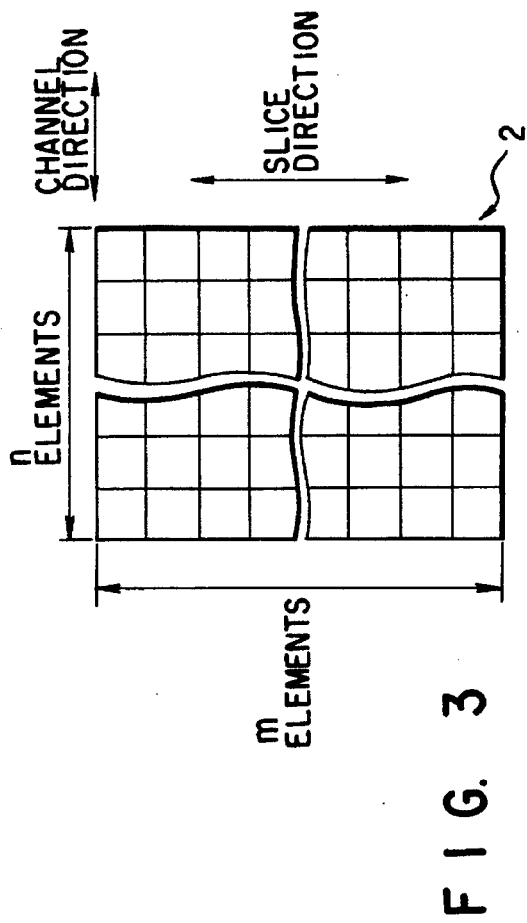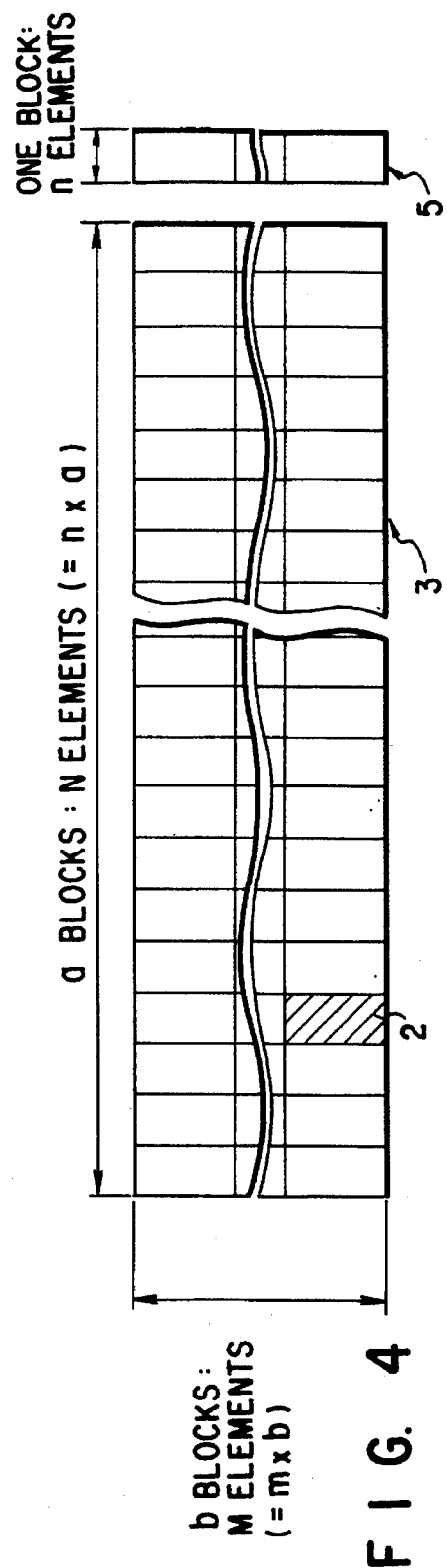

COMPUTED TOMOGRAPHY APPARATUS

BACKGROUND OF THE INVENTION

1. Field of the Invention

The present invention relates to a computed tomography apparatus (hereinafter simply called "CT apparatus") which obtains the tomographic images of a subject body to be examined.

2. Description of the Related Art

CT apparatuses are very popular medical diagnosis apparatuses. The third generation CT apparatus, the currently popular type, has an X-ray tube for generating an X-ray fan beam, which is flat to match with each slice of a subject body and spreads in a fan shape in each slice, and an X-ray detector which has multiple small X-ray detection elements aligned in a line over the area where this fan beam spreads. The X-ray tube and the X-ray detector face each other with the subject body in between. As the X-ray tube and the X-ray detector as a pair are moved around a subject body, a fan beam is irradiated on the subject body. During the irradiation of the fan beam, the fan beam which has passed the subject body is detected to acquire projection data from various directions around a slice. The projection data of 360 degrees around a slice is subjected to some computation using a predetermined image reconstruction algorithm to obtain the tomographic image of the subject body.

To obtain a reconstructed image with high precision, it is necessary to equalize the detected values of all the detection elements. Therefore, in the conventional apparatus, there is provided a sub detector for detecting an X-ray beam which is not passed through the subject body in addition to a main detector for detecting the X-ray beam which is passed through the subject body. The outputs of the detection elements of the main detector are corrected in accordance with the output of the sub detector so that the outputs of the detection elements of the main detector are made equal where the subject is not exist between the X-ray tube and the X-ray detector.

Sliced units of a subject body are called "slices," and the thickness of each slice at the time of obtaining a single reconstruction image is called "slice thickness." If the detection elements constituting a detector are aligned in a line, the tomographic image of the subject body detectable at a time is a single slice, and such a detector is called a single-slice type detector. Recently, the use of a multi-slice type detector which comprises multiple lines of detection elements and can acquire multiple slices of projection data at a time has begun in order to shorten the scanning time. In the multi-slice type detector, however, it is not sufficient to correct the outputs of the main detectors in accordance with the output of the sub detector to obtain a reconstruction image with high precision.

In general, when the electron beam emitted from the cathode of the X-ray tube is incident on the side surface (inclined surface) of the rotary anode having a conical shape, X-ray beam is generated in the direction that intersects the irradiation direction of the electron beam at 90 degrees. The point of collision of the electron beam on the rotary anode is the focal point of the X-ray tube. When this point of collision of the electron beam onto the inclined surface of the rotary anode is shifted, the position of generation of the X-ray beam or the focal point is shifted in the axial direction of a subject body (hereinafter called "body-axis direction"). The shifts of the rotary anode, the cathode and the flying direction of the electron beam result in the shifting of the focal point. Since the position shifting occurs due to a temperature change, a chronological change, the wearout of the electrodes and the like, it is inevitable that the focal position varies finely during the acquisition of projection data, changing the intensity profile of the X-ray beam in the slice direction.

If the intensity profile of the X-ray beam in the slice direction varies, the amount of X-ray beam incident to a specific line of multi-slice type detection elements may increases or the amount of X-ray beam may decrease for another line of detection elements. Even if the variation in the line of detection elements is corrected by using the sub detector, the variation in the lines is present. In the CT apparatus using a multi-slice type detector, to reduce the effective slice thickness of a reconstruction image, not only projection data from the detection elements associated with the corresponding slice but also projection data from the detection elements associated with different slices may be used to reconstruct the single slice of interest. If the output of a specific line of the detection elements is too large or too small, even when the sensitivity profile of the detector in the direction of the body-axis direction (slice direction) does not vary, an artifact (false image) is produced in the reconstruction image. The artifact reduces the quality of the reconstruction image and presents a poor image. Therefore, there is a strong demand for some ways of overcoming the conventional shortcoming of CT apparatuses using a multi-slice type detector, which originates from the shifting of the focal point, and improving the quality of reconstruction images.

SUMMARY OF THE INVENTION

Accordingly, it is an object of the present invention to provide a computed tomography apparatus using a multi-slice type detector, which can compensate for a change in projection data for each slice caused by a change in the radiation profile on the detector's surface in the slice direction due to the shifting of a focal point or the like, thus preventing an artifact from being produced in a reconstruction image.

According to the present invention, there is provided a computed tomography apparatus comprises means for irradiating radiation rays on slices of a subject body to be examined; detector means including multiple lines of detection elements arranged in association with the slices and receiving the radiation rays irradiated from the irradiating means to detect radiation ray transmission data of the slices; means for measuring an intensity distribution of the radiation rays, irradiated from the irradiating means, in a direction perpendicular to the slice; and means for compensating the radiation ray transmission data slice by slice in accordance with the intensity distribution measured by the intensity distribution measuring means.

The present invention therefore provides a multislice type CT apparatus which compensates the output of the detector means for detecting radiation ray transmission data of the slices for each line of detections in accordance with the intensity distribution of the radiation rays, so that even if the radiation ray profile on the detection's surface of the detector means in the slice direction is changed due to the shifting of the focal point or the like, it is possible to prevent projection data for each slice from changing in accordance with the change in the radiation ray profile, thus preventing the production of artifacts in reconstruction images.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 1 is a perspective view of a detector for use in a CT apparatus embodying the present invention;

FIG. 2 is a front view of the detector shown in FIG. 1;

FIG. 3 is a diagram showing a detection block as one structural unit of the detector shown in FIG. 1;

FIG. 4 is a plan view of the detector shown in FIG. 1;

DETAILED DESCRIPTION OF THE PREFERRED EMBODIMENTS

Figure 5:
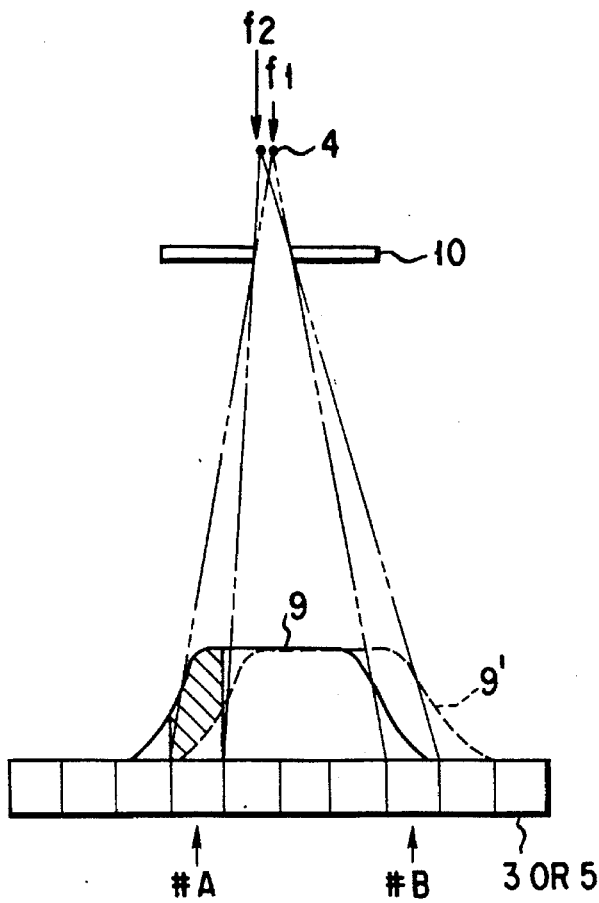
FIG. 5 is a side view of the detector shown in FIG. 1, illustrating a change in the X-ray profile in the slice direction based on the shifting of the focal point of an X-ray tube.

A preferred embodiment of a CT apparatus according to the present invention will now be described with reference to the accompanying drawings.

First Embodiment

To begin with, the principle of the first embodiment will be described. This embodiment includes a profile detector capable of measuring the intensity distribution (X-ray profile) in the slice direction of the X-ray fan beam emitted from an X-ray tube in addition to a multi-slice type main detector which can simultaneously detect projection data of a plurality of slices, and compensates for a change in the X-ray profile slice by slice with respect to the projection data of a plurality of slices obtained by the main detector. This scheme can prevent CT values from being shifted due to the shifting of the focal point of the X-ray in the body-axis direction.

FIG. 1 is a perspective view showing the structure of the detector according to this embodiment, and FIG. 2 is a front view as seen from the direction of II. As shown in FIGS. 1 and 2, a main detector 3 is a multi-slice type detector having multiple detection elements (X-ray detecting elements) arranged in a plurality of rows in the slice direction (the body-axis direction) and a plurality of columns in the channel direction (the arcuate direction) in order to detect an X-ray fan beam, which has been irradiated from an X-ray focal point 4 with a predetermined fan angle within a slice and a predetermined thickness in the slice direction (direction perpendicular to the surface of the sheet of FIG. 2) so as to acquire projection data of a plurality of slices at a time. As the main detector 3 is rotated in a predetermined orbital locus around a rotational center 0 in synchronous with the X-ray tube (only the focal point 4 is indicated as a point though the tube itself is not illustrated) while facing the X-ray tube, the main detector 3 can scan the subject body with an X-ray fan beam and acquire projection data of 360 degrees around a slice. Each row of detection elements of the main detector 3 are arranged in such a way that their X-ray incident sides are curved along the orbital locus around the focal point 4 of the X-ray tube so as to set the distances to the X-ray tube (focal point 4) from the detection elements equal to one another.

A profile detector 5 for detecting an X-ray fan beam that does not pass a subject body 7 (which is the circle indicating the maximum imageable range in FIG. 2) is provided in the vicinity of the main detector 3. The profile detector 5 is also synchronously rotated together with the main detector 3 while facing the X-ray tube, and each row of detection elements of this profile detector 5 are arranged in such a way that their X-ray incident sides are curved along the orbital locus around the focal point 4 of the X-ray tube where the associated row of detection elements of the main detector 3 are aligned, so that the distances to the X-ray tube (focal point 4) from the detection elements become the same. With this arrangement, the profile detector 5 can detect the intensity of the radiated X-ray beam from the X-ray tube for each slice. As apparent from the above, the profile detector 5 like the main detector 3 should comprise a plurality of rows of detection elements. The number of rows should not however exactly be the same as that of the main detector 3, and may be smaller than the latter. In this case, the intensity of the X-ray beam for each row of the main detector 3 should be acquired through interpolation. In this respect, the profile detector 5 has only to include two rows of detection elements. The profile detector 5 may comprise more rows of detection elements than the main detector 3 in order to improve the compensation precision. In FIG. 1, the profile detector 5 also have multiple columns of detection elements in the channel direction. Because the intensity data for compensation is not separated in the channel direction but is entirely added in the channel direction before being output, a single detection element may be sufficient in the channel direction. Since an X-ray path XPp which does not include the subject body 7 should be secured, a collimator 8 is provided on the X-ray incident side of the profile detector 5 and an upper slit 10 is provided on the irradiating side of the X-ray tube to restrict the X-ray irradiation area. The collimator 8 prevents the diffused X-ray from the subject body 7 from entering the profile detector 5. To positively eliminate the diffused X-ray, the diffused X-ray compensation as described in the Japanese patent by the present assignee (Jpn. Pat. Appln. KOKOKU No. 5-60930) entitled "X-RAY CT APPARATUS" may be performed. The diffused X-ray compensating apparatus disclosed in this patent publication comprises a main detector having a line of detection elements aligned at predetermined pitches, a diffused X-ray detector having fewer detection elements than the detection elements of the main detector, aligned at a different slice position than the main detector and at narrower pitches than the pitches of the main detector, an interpolation circuit for acquiring, through interpolation, diffused X-ray data between detected diffused X-ray data for the individual detection elements of the diffused X-ray detector, and a data processor for subtracting the detected diffused X-ray data for each detection element, obtained by the interpolation circuit, from the output of each detection element of the main detector. This structure allows the X-ray profile in the slice direction to be measured with less or without influence of the diffused X-ray.

The small detection elements are not manufactured one by one, but are manufactured as a detection block 2 consisting of n×m elements as shown in FIG. 3. Multiple detection blocks 2 are aligned in rows and columns as shown in FIG. 4, constituting each detector (the main detector or the sub detector). Each detection block 2 consists of "m" elements in the slice direction and "n" elements in the channel direction; one element is equivalent to one channel. The main detector 3 has "b" blocks in the slice direction and "a" blocks in the channel direction. That is, the main detector 3 has M (m×b) detection elements in the slice direction and N (n×a) detection elements in the channel direction. The profile detector 5 has "b" blocks in the slice direction and one block in the channel direction. That is, the profile detector 5 has M (m×b) detection elements in the slice direction and "n" detection elements in the channel direction.

Although the profile detector 5 is located on one side of the main detector 3 at a predetermined distance therebetween in the illustrated example, it may be arranged adjacent to the main detector 3 with a reduced distance therebetween or may be provided on both sides of the main detector 3. Although the main detector 3 and the profile detector 5 are constructed as separate detectors on separate substrates in the illustrated example, they may be integrated on the same substrate so that most of the integral unit is used as the main detector and only one end portion is used as the profile detector. The integral structure can eliminate a positional misalignment between the main detector and the profile detector and can ensure more accurate profile compensation.

FIG. 5 shows the detector in FIG. 2 from the direction V.

To compensate for a variation in the X-ray profile, first, the intensity at the reference timing before scanning should be measured. The X-ray profile is monitored during actual imaging, and data passing the subject body, output from the main detector 3, is then compensated in accordance with a change in the X-ray profile. It is assumed that the focal point 4 of the X-ray tube at the time a reference profile has been measured is at position f1 and it is shifted to position f2 at the time of scanning the subject body. Then, the profile of the fan beam incident to the detectors 3 and 5 changes to a broken line 9' from a solid line 9. That is, as the focal point 4 of the X-ray tube is shifted to f2 from f1, the irradiation area is shifted in the opposite direction to the actual shifting of the focal point with the position of the slit 10 as a fulcrum point because the fan beam is emitted through the slit 10 located on the X-ray irradiating side of the X-ray tube. As a result, at the time the subject body is scanned, the amount of incident X-ray becomes smaller for the row A (the shaded portion is the reduced amount) and becomes greater for the row B than those obtained at the reference timing. The row-by-row change in the amount of incident X-ray likely occurs for the main detector 3 and the profile detector 5 which are so arranged that the slice positions are associated with each other. That is, the output data of the profile detection elements corresponding to the row A in the main detector 3 changes in the same manner as the output of the row A of the main detector 3. The same is true of the row B and the other rows. It is therefore possible to compensate for a change in the X-ray intensity for each row caused by the shifting of the focal point of the X-ray tube to convert the intensity data to transmission data for the same amount of incident X-ray as is provided at the reference timing by compensating the output of the main detector 3 in such a way that the ratio of the output of the profile detector 5 at the reference timing to the same output at the time of scanning the subject body becomes constant for all the rows of the main detector 3.

The specific structure of a CT apparatus according to the first embodiment of the present invention which employs the above-described principle will be discussed below.

Figure 6:
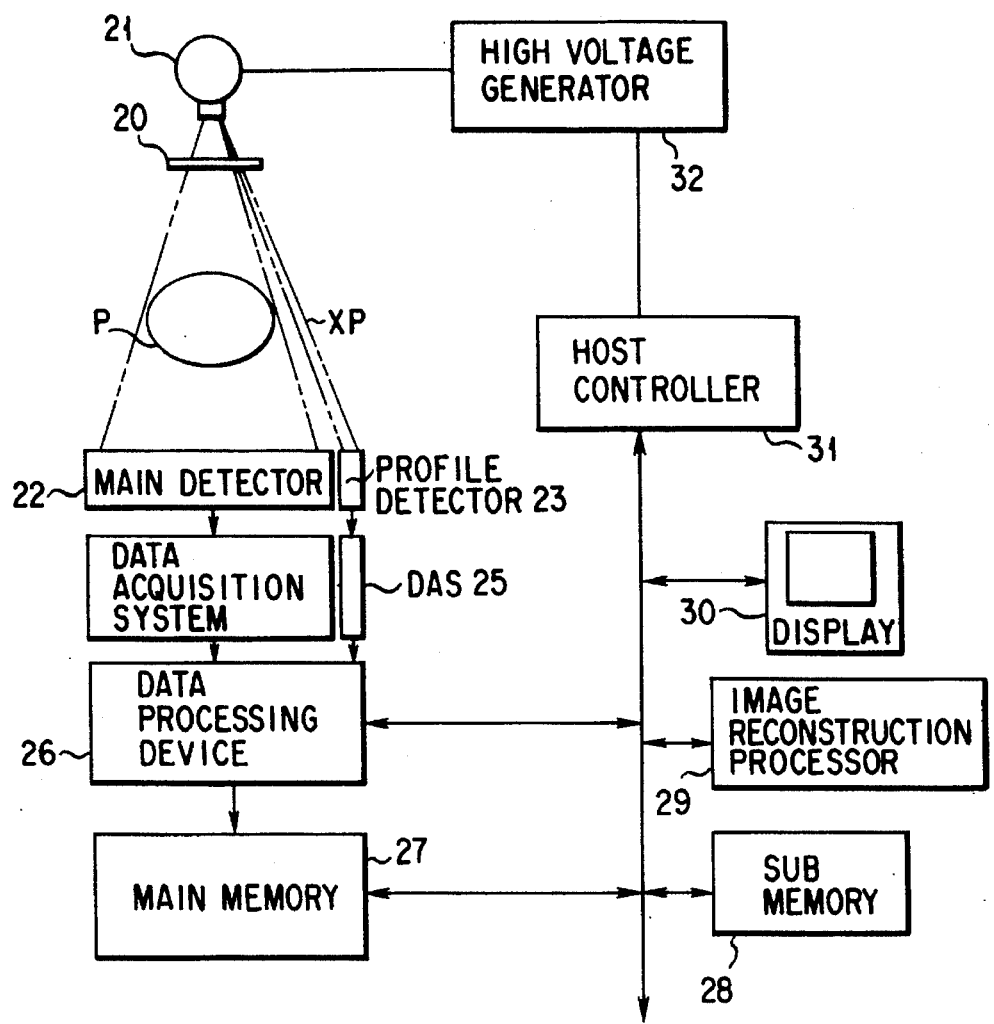
FIG. 6 is a block diagram showing an example of the system structure of a CT apparatus according to a first embodiment of the present invention.

FIG. 6 presents a block diagram of the system structure of this CT apparatus. In FIG. 6, "20" denotes a slit, "21" denotes an X-ray tube, "22" is a main detector and "23" is a profile detector. Those detectors 22 and 23 have the same structures as the main detector 3 and the profile detector 5 which have been discussed above with reference to FIGS. 1 through 4. It is to be noted that the collimator in front of the profile detector 23 is not shown in FIG. 6.

In the diagram, "24" is a data acquisition system for the main detector, "25" is a data acquisition system for the profile detector, "26" is a data processing device, "27" is a main memory 27, "28" is a sub memory, "29" is an image reconstruction processor, "30" is a display, "31" is a host controller, and "32" is high voltage generator. This CT apparatus of course includes a driving mechanism for moving the X-ray tube 21, the main detector 22, and profile detector 23 along a predetermined orbital locus, a control system for this driving mechanism, and an operation console for operating the system, though not illustrated.

The data acquisition system 24 for the main detector 22 acquires channel data for each slice position (projection data for each X-ray path for each slice position) based on each slice position of the main detector 22 and a detection signal corresponding to the X-ray intensity detected by the detection elements for each channel position. The data acquisition system 25 for the profile detector 25 acquires intensity distribution (profile data) for each slice position based on each slice position of the profile detector 23 and a detection signal corresponding to the X-ray intensity detected by the detection elements for each channel position. The data processing device 26 performs various preprocesses such as compensation and normalization of channel data for each slice position using the intensity distribution data.

The main memory 27 stores the preprocessed channel data for each slice position, the image reconstruction processor 29 reconstructs an X-ray absorption based image on the basis of the data stored in the main memory 27, and the sub memory 28 holds the reconstruction image data and the like. The display 30 is capable of displaying the reconstruction image, an operation screen for entering various commands, and images and characters used to display a data input screen or the like.

The host controller 31 is the central processing unit which performs the general control of the system. The high voltage generator 32 supplies a desired high voltage to the X-ray tube 21 to generate X-ray, and controls the current as well as the desired voltage.

This CT apparatus further includes a scan driving system for turning the X-ray tube 21 and a detecting device (the main detector 22 and the profile detector 23) around the subject body to scan the subject body and an operation console for performing various operations, though not illustrated.

The operation of the thus constituted first embodiment will now be described. A fan beam is irradiated from the X-ray tube 21 while rotating the X-ray tube 21, the main detector 22 and the profile detector 23 in a predetermined direction to scan the subject body and projection data of a cross section (slice) of the subject body is acquired. Before executing this scanning, reference data for compensating the X-ray profile in the slice direction should have been collected.

The data output from the main detector 22 and the profile detector 23 are respectively sent to the data acquisition system 24 for the main detector and the data acquisition system 25 for the profile detector to be preprocessed for each slice, yielding projection data. Those projection data are stored via the data processing device 26 into the main memory 27 as reference data.

As described above, the X-ray path XPp which does not pass the subject body is secured for the profile detector 23. Further, the diffused X-ray from the subject body is removed by the collimator from the X-ray to be incident to the profile detector 23. Alternatively, if the diffused X-ray compensation is performed, the X-ray profile ("9" in FIG. 5) of the fan beam in the body-axis direction, which has been limited by the slit 20, has passed the subject body and then has entered the main detector 22 is measured with a reduced influence of the diffused X-ray even if the collimator is not provided.

As a result, a fan beam is incident to a narrower range than the slice width of the main detector 22 having the detection performance for a total of M slices, as shown in FIG. 5, so that the profile of the fan beam incident to the detector can be detected and monitored by the profile detector 23.

When the focal point of the X-ray tube is shifted between the time of acquiring the reference data and the time of scanning the subject body (from f1 to f2), the profile of the fan beam incident to the detector changes to the broken line 9' from the solid line 9 in FIG. 5. At the time of scanning the subject body, therefore, the amount of incident X-ray becomes smaller for the detection elements of the row A (the shaded portion is the reduced amount) and becomes greater for the detection elements of the row B than those obtained at the time of acquiring the reference data. The row-by-row change in the amount of incident X-ray likely occurs for the main detector 22 (3 in FIG. 5) and the profile detector 23 (5 in FIG. 5), and the output data of the profile detection elements corresponding to the row A changes in the same manner as the output of the row A of the main detector 22. For all the rows of the main detector 22 (all the slice positions detectable by the detector 22 itself), therefore, the ratio of the current output data of the profile detector for the associated rows to the reference data is obtained and the current projection data is compensated based on this ratio. Consequently, the data of the incident X-ray detected by the individual rows of the main detector 22 can be converted to that for the same amount of incident X-ray as that detected at the time of acquiring the reference data.

It is assumed that the detected output data for an "i" channel at a "j" slice position in the main detector 22 before compensation is $MAIN_{ij}$ and the detected output data after compensation is $MAIN'_{ij}$, compensation can be executed from the following equation.

$$MAIN'_{ij} = MAIN_{ij} \times (PROF_j(ini)/PROF_j(scan))$$

where $PROF_j(ini)$ is the output data of the j row of the profile detector 23 at the time of acquiring the reference data and $PROF_j(scan)$ is the output data of the j row of the profile detector 23 at the time of scanning the subject body.

By allowing the data processing device 26 to compensate the data, detected by the main detector 22 at the time of scanning the subject body, based on the above equation using the output of the profile detector 23, the present CT apparatus can compensate for a change in the X-ray profile in the slice direction in such a way as to set its characteristic to the same characteristic obtained at the time of acquiring reference data, thus preventing projection data for each slice in the multi-slice type detector from changing due to a change in the X-ray profile in the slice direction.

Figure 7:
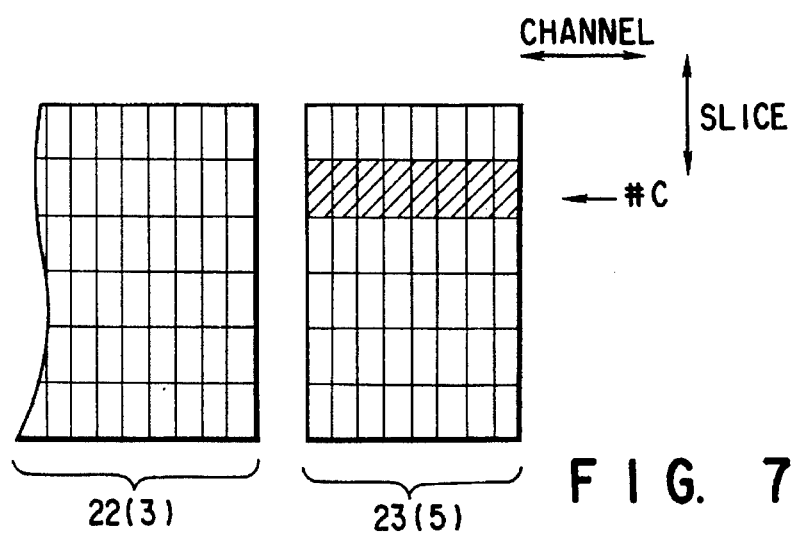
FIG. 7 is a detailed diagram of a profile detector in the first embodiment.

Because each detector is constituted using the detection blocks 2 in this embodiment as shown in FIGS. 3 and 4, the profile detector 23 is designed to have a plurality of channels for one row as shown in FIG. 7. In measuring the X-ray profile, however, data of a plurality of channels are grouped row by row and are used as data of one row. In FIG. 7, the profile detector 23 has the structure of 6 rows×8 channels, so that, for example, the shaded portions of the data of the second row (row C) are grouped into single data. The grouping may be accomplished by the hardware basis such as modifying the detection blocks 2, or may be accomplished by acquiring individual pieces of data and then grouping them through computation by software. Securing the X-ray path for the profile detection elements and/or grouping data in the channel (ch) direction can improve the S/N ratio in one row of data.

Figure 8:
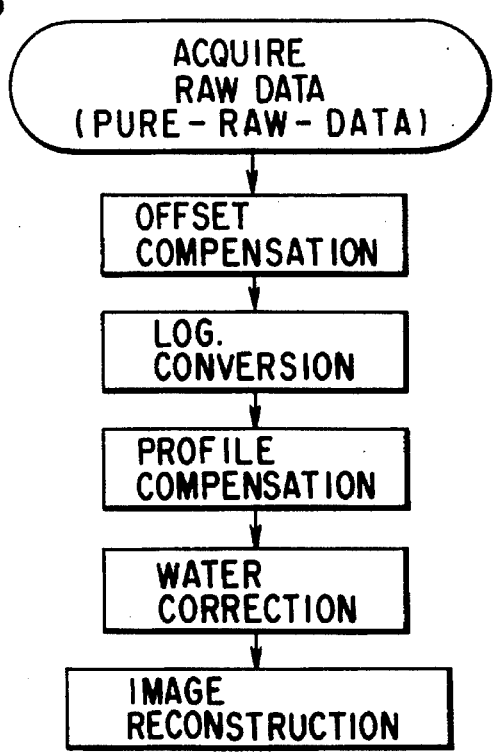
FIG. 8 is a flowchart for explaining the operation of the first embodiment.

Various kinds of data for compensation and projection data of the subject body obtained in the above manner are subjected to the processing as shown in FIG. 8 by the data processing device 26 in FIG. 6, thus yielding compensated projection data.

More specifically, after offset compensation is performed on projection data acquired at the time of scanning the subject body and logarithm conversion is performed on each projection data, a change in the X-ray profile in the slice direction is compensated based on the X-ray intensity data from the profile detector 23 for each slice position (row position) and then water correction is performed to acquire the difference between the X-ray absorption with water disposed therebetween and the X-ray absorption without water. The resultant projection data is then output as compensated projection data. This compensated projection data is stored in the main memory 27. The compensated projection data of a slice of the subject body is subjected to reconstruction computation by the image reconstruction processor 29, and the reconstruction image reflects no influence of the shifting of the focal point, so that an excellent tomographic image without artifacts can be observed.

As described above, this embodiment can provide a CT apparatus in which the profile detector which has the same rows of detection elements and the same width in the slice direction as the main detector and which detects the X-ray that do not pass a subject body is provided, whereby a change in the X-ray profile in the slice direction is monitored by the profile detector and the detected data from the main detector is compensated for each row of detection elements (each slice position) in association with a change in this profile. Even when the focal point of the X-ray tube is shifted, changing the X-ray profile in the slice direction, this change can be grasped and compensated properly, thus providing excellent reconstruction images without artifacts.

Other embodiments of the CT apparatus according to the present invention will be described. The same portions as those of the first embodiment will be indicated in the same reference numerals and their detailed description will be omitted.

Second Embodiment

Figure 9:
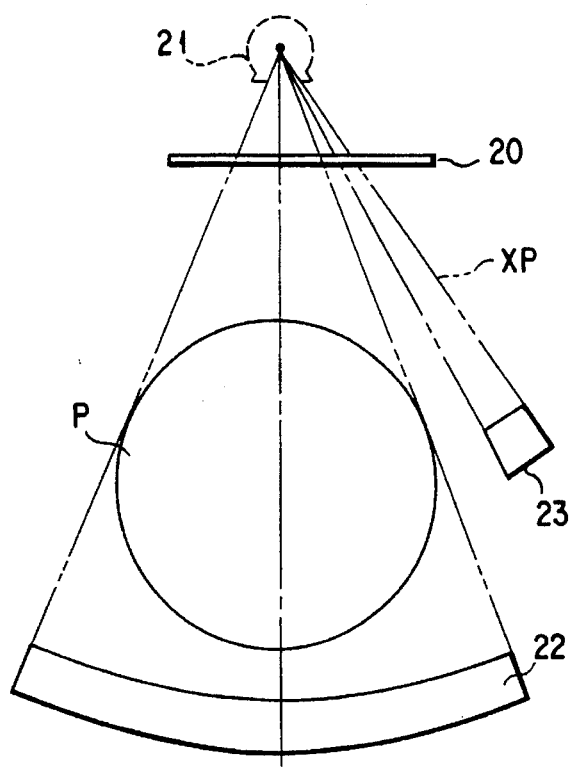
FIG. 9 is a front view exemplifying the arrangement of a detector in a CT apparatus according to a second embodiment of the present invention.

In the first embodiment, the main detector and the profile detector are arranged on the same orbital locus on the assumption that the main detector and the profile detector in use have the same specifications. The main detector and the profile detector may have different specifications or may be located at different distances from the focal point of the X-ray tube as long as the X-ray intensity for each row of the main detector can be measured. In some case, one may request to change the distances of the main detector and the profile detector from the focal point of the X-ray tube because no sufficient installing space is secured for the profile detector on the same orbital locus of the main detector or some other reasons. The second embodiment is designed to meet such a demand, and has the profile detector 23 arranged significantly closer to the X-ray tube 21 than the main detector 22 as shown in FIG. 9.

Figure 10:
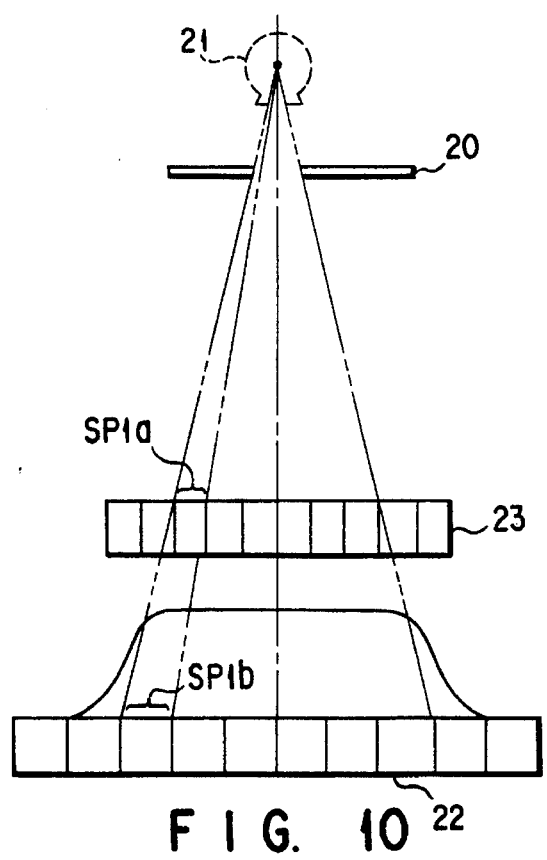
FIG. 10 is a side view exemplifying the arrangement of the detector in the second embodiment.

In this case, although the intensity of the fan beam incident to the profile detector 23 and the width of one slice differ from those for the main detector 22 from the optical positional relationship, the same advantages as obtained by the first embodiment can be provided by adjusting the slice pitch of the profile detector 23 as shown in FIG. 10 in accordance with the distance from the focal point of the X-ray tube 21. More specifically, the slice pitch SP1a of the profile detector 23 should be adjusted in accordance with the distance from the X-ray tube in such a way as to be coincident with the slice pitch SP1b of the main detector, from the geometrical relationship of the fan beam that spreads from the focal point at a predetermined angle. Further, even if the number of slices of the profile detector 23 is less than that of the main detector 22, a sufficient effect can be expected as long as the profile on the main detector 22 can be measured at an allowable precision.

The present invention can also be adapted for the case where the distance of the main detector 22 from the focal point of the X-ray tube is different from that of the profile detector 23, and can properly detect and compensate for the shifting of the focal point of the X-ray tube, thereby providing artifactless excellent reconstruction images.

As described in detail above, the present invention can provide a CT apparatus in which the profile detector which has the same rows of detection elements and the same width in the slice direction as the multi-slice type main detector and which detects the X-ray that do not pass a subject body is provided, whereby a change in the X-ray profile in the slice direction is monitored by the profile detector and the detected data from the main detector is compensated in association with a change in this profile. Even when the focal point of the X-ray tube is shifted, changing the X-ray profile in the slice direction, this change can be detected and compensated properly, thus providing artifactless excellent reconstruction images.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the present invention may be adapted to not only the structure which uses an X-ray tube as the X-ray source but also to the structure which another type of radiation ray source.

What is claimed is:

1. A computed tomography apparatus comprising:
   means for irradiating radiation ray on slices of a subject body;
   detector means, including multiple lines of detection elements arranged in association with said slices, for receiving radiation ray irradiated from said irradiating means to detect radiation ray transmission data of said slices;
   means for measuring an intensity distribution of radiation ray, irradiated from said irradiating means, in a direction perpendicular to the slices; and
   means for compensating said radiation ray transmission data slice by slice in accordance with said intensity distribution measured by said measuring means.

2. The computed tomography apparatus according to claim 1, wherein said intensity distribution measuring means is located at a distance from said irradiating means equal to a distance of said detector means therefrom, and comprises rows of detection elements equal in number to said detection elements of said detector means.

3. The computed tomography apparatus according to claim 1, wherein said intensity distribution measuring means is located at a distance from said irradiating means equal to a distance of said detector means therefrom, and comprises rows of detection elements fewer in number than said detection elements of said detector means, and means for acquiring an intensity distribution of radiation ray at each row of said detector means by interpolation.

4. The computed tomography apparatus according to claim 1, wherein said intensity distribution measuring means is located at a distance from said irradiating means different from a distance of said detector means therefrom, and comprises rows of detection elements equal in number to said detection elements of said detector means, and a row pitch of said intensity distribution measuring means is set in accordance with a ratio of said distance between said irradiating means and said detector means to said distance between said irradiating means and said intensity distribution measuring means and a row pitch of said detection elements of said detector means.

5. The computed tomography apparatus according to claim 4, wherein said intensity distribution measuring means is located closer to said irradiating means than said detector means, and comprises rows of detection elements equal in number to said detection elements of said detector means, and said row pitch of said intensity distribution measuring means is smaller than said row pitch of said detection elements of said detector means.

6. The computed tomography apparatus according to claim 1, wherein said detector means and said intensity distribution measuring means are constituted by arranging detection element blocks in a matrix form, said detector means outputs radiation ray transmission data for each detection element, and said intensity distribution measuring means outputs intensity data for each row.

7. The computed tomography apparatus according to claim 1, wherein said detector means and said intensity distribution measuring means are formed adjacent to each other on a same substrate.

8. The computed tomography apparatus according to claim 1, wherein said detector means and said intensity distribution measuring means are formed apart from each other on a same substrate.

9. The computed tomography apparatus according to claim 1, wherein said detector means and said intensity distribution measuring means are on separate substrates located adjacent to each other.

10. The computed tomography apparatus according to claim 1, wherein said detector means and said intensity distribution measuring means are on separate substrates set apart from each other.

11. The computed tomography apparatus according to claim 1, wherein said intensity distribution measuring means is provided on one end of a row extending from each row of detection elements of said detector means.

12. The computed tomography apparatus according to claim 1, wherein said intensity distribution measuring means is provided on both ends of a row extending from each row of detection elements of said detector means.

13. The computed tomography apparatus according to claim 1, wherein said intensity distribution measuring means has a collimator facing said irradiating means for eliminating radiation ray having passed a subject body.

14. The computed tomography apparatus according to claim 1, wherein said compensation means obtains a ratio of a reference value PROF(ini) of an output of said intensity distribution measuring means to a current value PROF(scan) and compensates a current value MAIN of said detector means as follows in accordance with said ratio:

$$MAIN' = MAIN \times PROF(ini)/PROF(scan)$$

where MAIN' is a value after compensation.

* * * * *